United States Patent [19]

Ungerer et al.

[11] Patent Number: 4,975,418
[45] Date of Patent: Dec. 4, 1990

[54] THERAPEUTICALLY ACTIVE COMPOSITIONS OF PSEUDO-PEPTIDE OF GLUTAMYL-ASPARTIC ACID

[75] Inventors: Arielle Ungerer; Jean De Barry; Yves L. J. Boulanger; Monique Schmitz-Bourgeois, all of Strasbourg, France

[73] Assignee: Centre National de la Recherche Scientific (CNRS), Paris, France

[21] Appl. No.: 153,834

[22] PCT Filed: May 7, 1987

[86] PCT No.: PCT/FR87/00151
 § 371 Date: Jan. 11, 1988
 § 102(e) Date: Jan. 11, 1988

[87] PCT Pub. No.: WO87/06931
 PCT Pub. Date: Nov. 19, 1987

[30] Foreign Application Priority Data

May 9, 1986 [FR] France ................ 86 06704

[51] Int. Cl.$^5$ .................. A61K 37/02; C07C 5/06
[52] U.S. Cl. .............................. 514/19; 514/18; 530/331; 562/565
[58] Field of Search ............ 514/19, 18; 530/331; 562/565

[56] References Cited

U.S. PATENT DOCUMENTS

| | | | |
|---|---|---|---|
| 2,500,019 | 3/1950 | Bersworth | 562/565 |
| 4,161,522 | 7/1979 | Hamburger | 514/18 |
| 4,585,757 | 4/1986 | Pang et al. | 514/18 |
| 4,761,495 | 8/1988 | Wirth et al. | 562/565 |

OTHER PUBLICATIONS

Utsumi, Chemical Abstracts (1963) 59:3032a.
Cheung et al., Chemical Abstracts (1979) 91:118993h.
Anderson et al., Chemical Abstracts (1986) 105:127416g.
Rodin et al., Chemical Abstracts (1973) 78:136706c.
CA vol. 77 (1972):85649f Fowden.
CA vol. 80 (1974):93155u Kasai et al.
CA vol. 82 (1975):121068e Kasai et al.
CA vol. 83 (1975):175494e Kasai et al.
CA vol. 94 (1981):188659q Kasai et al. (Takanori).
CA vol. 104 (1986):203870x Kasai et al.

*Primary Examiner*—Lester L. Lee
*Attorney, Agent, or Firm*—Bertram I. Rowland; Richard L. Neeley

[57] ABSTRACT

Therapeutically active pseudo-peptide characterized in that it comprises at least the sequence of the γ-glutamyl-aspartic acid or one of its derivatives. Said pseudo-peptide may be used in the preparation of a pharmaceutical composition useful particularly in the treatment of epilepsy or affections of the central nervous system in general.

5 Claims, No Drawings

THERAPEUTICALLY ACTIVE COMPOSITIONS OF PSEUDO-PEPTIDE OF GLUTAMYL-ASPARTIC ACID

The present invention relates to novel therapeutically active pseudo-peptides useful particularly in the treatment of disorders of the central nervous system such as epilepsy and failures of memory associated with certain degenerative diseases.

The importance of chemical mediators in disorders of the central nervous system (CNS) is known.

Among the latter a distinction is made between inhibitory neurotransmitters such as GABA (gamma-aminobutyric acid) and serotonin, and excitatory neurotransmitters such as histamine, dopamine and glutamic acid.

These latter are more particularly concerned by the present invention, especially the glutamatergic system which acts at different levels of the brain and very probably plays an important role in the mechanisms implicated in the retention of memory (BLISS, DOLPHIN, 1982; ECCLES, 1983; COLLINGRIDE, 1985).

As a matter of fact, the present invention relates to the agonist or antagonist properties of novel pseudo-peptides on neurotransmission, particularly at the level of the glutamatergic system.

Involved are novel pseudo-peptides comprising at least the sequence of γ-glutamyl-aspartic acid as well as derivatives of these pseudo-peptides. Among these pseudo-peptides mention should be made of the acid itself as well as the tripeptides corresponding to an additional amino acid linked to the C-terminal end. The derivatives in question are essentially salts, esters and amides, quaternary amine derivatives as well as cyclic derivatives with pharmaceutically acceptable acidic and basic substances and alcohols.

Preferably, according to the invention, this novel pseudo-peptide is N-γ-glutamyl-aspartic acid itself or one of its derivatives. These substances may exist in any isomeric form, namely they may be in the form of N-γ-L-glutamyl-L-aspartic acid, N-γ-L-glutamyl-D-aspartic acid, N-γ-D-glutamyl-L-aspartic acid or N-γ-D-glutamyl-D-aspartic acid.

A very especially preferred substance according to the present invention is N-γ-L-glutamyl-L-aspartate, the formula of which is the following:

$$\begin{array}{c}HOOC\\ \phantom{HOOC}\diagdown\\ \phantom{HOOCC}CH-CH_2-CH_2-\overset{O}{\overset{\|}{C}}-NH-CH-CH_2-COOH\\ \phantom{HOOC}\diagup \phantom{CH-CH_2-CH_2-C-NH-}|\\ H_2N \phantom{CH-CH_2-CH_2-C-NH-CH}COOH\end{array} \quad (I)$$

Interesting results have also been obtained with the N-γ-D-glutamyl-D-aspartic acid form.

Another particularly useful pseudo-peptide according to the invention is N-γ-glutamyl-aspartyl-aspartic acid and its derivatives, substances in which each of the amino acids may exist in the right-handed (R, in accordance with the international nomenclature) or the left-handed form (S).

The preferred N-γ-glutamyl-aspartyl-aspartic acid according to the invention is that in which each of the amino acids is present in the left-handed form (S).

The synthesis of the pseudo-peptides according to the present invention can be carried out by the methods known to one skilled in the art of peptide synthesis.

Thus, the coupling of protected glutamic acid, the acidic function being activated if necessary, with protected aspartic acid can be carried out in the presence of a coupling agent such as N,N'-dicyclohexylcarbodiimide.

Similarly, in order to prepare N-γ-glutamyl-aspartyl-aspartic acid, one may start from the compound previously obtained by protecting or activating the appropriate functions and by coupling it to also protected aspartic acid.

These syntheses can be carried out in a solid phase or in an organic phase.

The final step in both of these procedures consists in removing the protecting group(s) by an appropriate technique in order to give rise to N-γ-glutamyl-aspartic acid and N-γ-glutamyl-aspartyl-aspartic acid, respectively, or their derivatives.

The pseudo-peptides according to the present invention are particularly useful for the preparation of a pharmaceutical composition.

This is the reason why the present invention relates to pharmaceutical compositions comprising, as active ingredient, at least one pseudo-peptide according to the invention. These pharmaceutical compositions are useful for the treatment of various diseases affecting the central nervous system, particularly epilepsy and memory disorders.

During the first stages of the preparation and development of epileptic drugs it is necessary to generate experimental convulsive crises in an animal. The experimental convulsive crises make it possible to identify anticonvulsants, the anti-epileptic properties of which will be subsequently verified.

That is the reason why convulsive crises are induced in the SWISS mouse by the intraperitoneal injection of pentylenetetrazole at a dose of about 85 mg/kg.

Pentylenetetrazole is a bulbar excitant which, at this dose, causes convulsive crises in the mouse and the rabbit in a classical fashion with several well-characterized stages.

The subsequent intraperitoneal administration of the substance of formula I according to the invention brought about a suppression of these crises under the following conditions:

suppression of crises in 50% of the animals at doses of 142.5 nmol/kg and 285 nmol/kg, suppression of crises in 70% of the animals at doses of 570 nmol/kg.

The subsequent intraperitoneal administration of N-γ-D-glutamyl-D-aspartic was also carried out and brought about the suppression of crises under the following conditions:

suppression of crises in 40% of the animals at a dose of 71 nmol/kg, suppression of crises in 60% of the animals at a dose of 285 nmol/kg.

The substances of the present invention are thus seen to be very active against convulsive crises caused by chemical excitation. At the doses used they are completely non-toxic.

Other assays (electrical excitation, audiogenic crisis, etc..) must be carried out and they will make it possible to determine the necessary doses of the anti-epileptic active principle(s) according to the present invention.

The present invention will be better understood by reading the following examples.

EXAMPLE 1

Process for the synthesis of
N-γ-L-glutamyl-L-aspartate of formula I

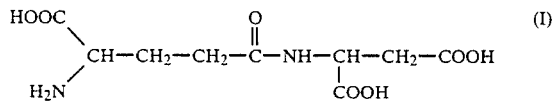

The starting materials were obtained from BACHEM A.G.. One mmole of triethylamine is added to a suspension of 0.5 mmole of N-benzyloxycarbonyl-L-glutamine benzyl ester and 0.5 mmole of L-aspartic dibenzyl ester p-tosylate in 10 ml of acetonitrile at 5° C. After stirring for 15 minutes, 0.5 mmole of N,N'-dicyclohexylcarbodiimide is added and the mixture is again stirred for 18 hours at 5° C. One drop of acetic acid is then added, followed by 25 ml of acetone, and the mixture is cooled for one hour, then filtered to remove the acylurea formed. After evaporation to dryness under vacuum, the residue is taken up in 50 ml of chloroform and the solution is washed successively with 1 N HCl (twice), water, 5% aqueous NaHCO$_3$ (twice), then water. The residue is dried in a rotary evaporator. The product obtained is then crystallized with ethyl acetate, then recrystallized from the system ethyl acetate/petroleum ether to give 0.35 g of protected peptide (72% yield) with a melting point of 121°–122° C.

200 mg of protected peptide are subjected to hydrogenation in 80% acetic acid over 100 mg of catalyst (palladium-active charcoal) for 18 hours. The catalyst is removed by filtration and the solution is evaporated to dryness under vacuum. The deprotected pseudo-peptide is crystallized and recrystallized from the system water/ethanol to give 41 mg of the compound of formula I (42% yield) with a melting point of 210°–212° C.

The pseudo-peptide obtained is then repurified by HPLC on a PRP 1 column (Hamilton) in a 10 mM aqueous solution of hexafluorobutyric acid containing 10% methanol.

EXAMPLE 2

Process for the synthesis of N-γ-D-glutamyl-D-aspartic acid

The methods used for the synthesis of γ-D-glutamyl-D-aspartic acid are identical with those of example 1, except that the reagents N-benzyloxycarbonyl-L-glutamic benzyl ester and L-aspartic dibenzyl ester p-tosylate are replaced by their right-handed equivalents (R) N-benzyloxycarbonyl-D-glutamic benzyl ester and D-aspartic dibenzyl ester p-tosylate.

EXAMPLE 3

Process for the characterization of the pseudo-peptides obtained in examples 1 and 2

The structure of these pseudo-peptides was established by biochemical methods, then confirmed by a mass spectrometric analysis.

Aspartic acid is the C-terminal acid. This was established by hydrazinolysis of the pseudo-peptide; hydrazine, H$_2$N-NH$_2$, cleaves peptide bonds and converts the amino acid residues into hydrazides, except for the one located at the C-terminal end which can be identified by means of the Durrum D500 amino acid analyser.

Labelling of the NH$_2$-terminal end of the pseudo-peptide by 1-dimethylaminonaphthalene-5-sulfonyl chloride (dansyl chloride or DNS-Cl) has made it possible to characterize the N-terminal residue: it is glutamic acid. On the other hand, negative results were obtained with 4-N,N-dimethylaminoarobenzene-4'-isothiocyanate (DABITC), the reagent used in the method of CHANG and which also reacts with the NH$_2$-terminal end of peptide chains and enables the N-terminal residue to be determined. However, the pseudo-peptide reacts with ninhydrin (blue colour) which implies that its NH$_2$-terminal end is free. These apparently contradictory results can only be explained by the existence of a peptide-like bond between the two amino acid constituting the pseudo-peptide, namely a linkage between the γ-carboxyl function of the N-terminal glutamic acid and the amine function of the C-terminal aspartic acid.

The optical isomerism of the amino acids of the two pseudo-peptides was confirmed by gas chromatography on a chiral phase.

We claim:

1. A pharmaceutical composition, comprising:
   (1) N-γ-glutamyl-aspartic acid in an amount sufficient for the treatment of deseases affecting the central nervous system selected from the group consisting of memory loss associated with degenerative neurological diseases and epilepsy convulsions, or its physiologically acceptable salts, esters, amides, and quaternary amine derivatives, or the cyclic imide derivative thereof, and
   (2) a pharmaceutically acceptable carrier.

2. A pharmaceutical composition according to claim 1, wherein said compound is N-γ-L-glutamyl-L-aspartic acid, N-γ-L-glutamyl-D-aspartic acid, N-γ-D-glutamyl-L-aspartic acid, and N-γ-D-glutamyl-D-aspartic acid.

3. A pharmaceutical composition according to claim 1, wherein said compound is N-γ-L-glutamyl-L-aspartic acid or a pharmaceutically acceptable salt, ester or cyclic imide derivative thereof.

4. A pharmaceutical composition according to claim 1, wherein said compound is N-γ-D-glutamyl-D-aspartic acid or a pharmaceutically acceptable salt, ester or cyclic imide derivative thereof.

5. A method for treating a host suffering from a central nervous system disorder selected from the group consisting of memory loss associated with degenerative neurological diseases and epilepsy convulsions, said method comprising:
   administering to said host an amount sufficient to treat said disorder of a composition according to any one of claims 1 to 4.

* * * * *

UNITED STATES PATENT AND TRADEMARK OFFICE
CERTIFICATE OF CORRECTION

PATENT NO. : 4,975,418
DATED : December 4, 1990
INVENTOR(S) : Ungerer, et. al.

It is certified that error appears in the above-identified patent and that said Letters Patent is hereby corrected as shown below:

On the Title page, item [73], "Scientific" should read

--Scientifique--.

Signed and Sealed this

Fifteenth Day of December, 1992

Attest:

DOUGLAS B. COMER

*Attesting Officer*    Acting Commissioner of Patents and Trademarks